United States Patent [19]

Mozell

[11] Patent Number: 4,771,484
[45] Date of Patent: Sep. 20, 1988

[54] WOMEN'S URINE CONDUCTING APPARATUS

[76] Inventor: Maxwell M. Mozell, 4594 S. Brookhill Dr., Manlius, N.Y. 13104

[21] Appl. No.: 917,703

[22] Filed: Oct. 10, 1986

[51] Int. Cl.$^4$ ............................................ A47K 11/00
[52] U.S. Cl. ................................................... 4/144.4
[58] Field of Search ........................ 4/144.1–144.4, 4/243; 128/760, 761, 767; 604/327–331, 347, 350, 354; 428/478.2

[56] References Cited

U.S. PATENT DOCUMENTS

| | | | |
|---|---|---|---|
| 854,593 | 5/1907 | Nelson | 604/330 |
| 1,746,162 | 2/1930 | Nickowitz | 428/478.2 |
| 1,962,338 | 6/1934 | Charch | 428/478.2 |
| 3,329,973 | 7/1967 | Bobbe | 4/144.4 X |
| 3,964,111 | 6/1976 | Packer | 4/144.4 |
| 4,202,058 | 5/1980 | Anderson | 4/144.3 |
| 4,568,339 | 2/1986 | Steer | 4/144.3 X |

Primary Examiner—Charles E. Phillips
Attorney, Agent, or Firm—Wall and Roehrig

[57] ABSTRACT

Apparatus for aiding a women while urinating in a standing position that includes a container having a rigid inner cup surrounded by a soft protective blanket. The blanket has a radially extended lip that is designed to contact the user's body to form a comfortable protection seal thereagainst. A liner made of water soluable gelatine is removably positioned in the container which consists of a collector for receiving urine and a tube extending from the lower part of the collector. The tube passes out of the container and is provided with sufficient length so that discharge urine can be directed away from the user's clothing.

12 Claims, 1 Drawing Sheet

U.S. Patent  Sep. 20, 1988  4,771,484
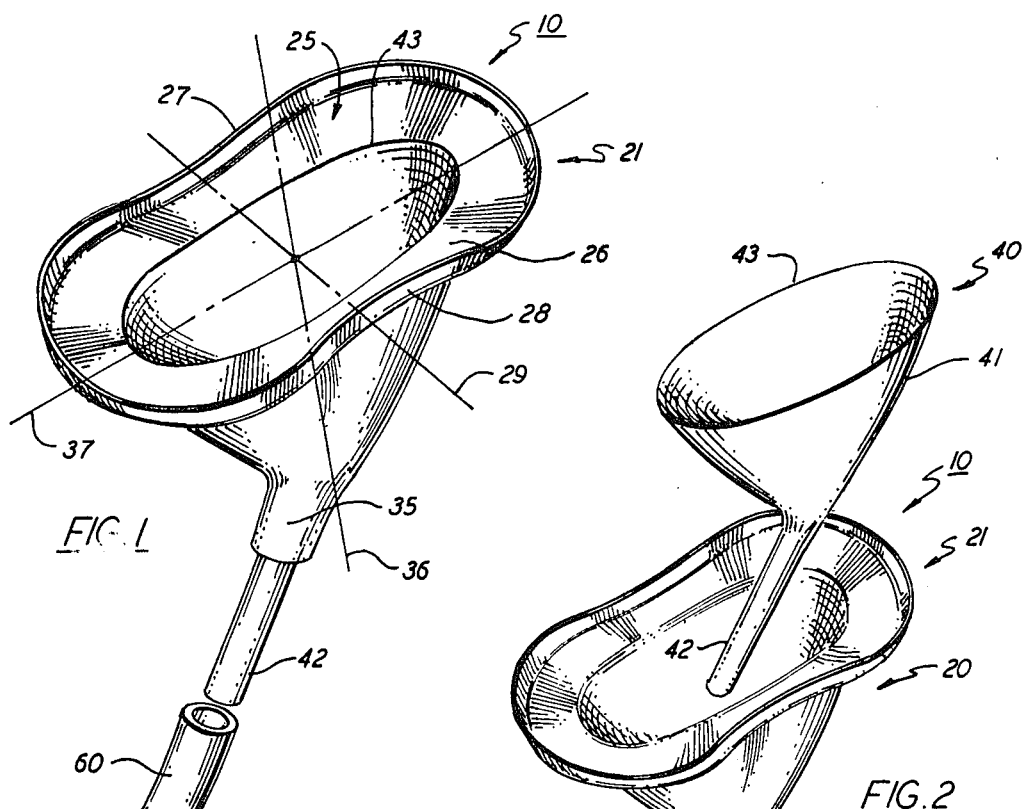
FIG. 1
FIG. 2
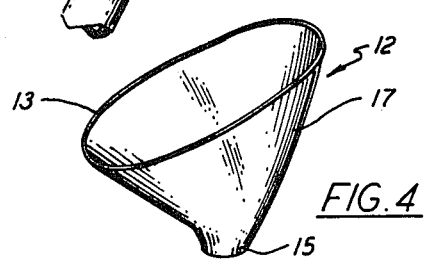
FIG. 4
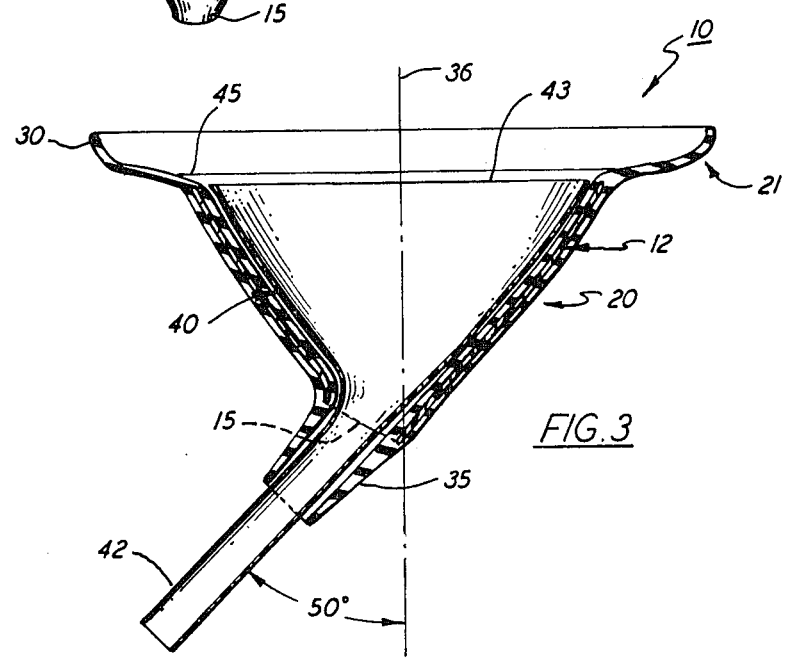
FIG. 3

WOMEN'S URINE CONDUCTING APPARATUS

BACKGROUND OF THE INVENTION

This invention relates to a device that enables a woman to safely and hygenically urinate while in a standing position. More particularly this invention relates to a portable device for external use that has a water soluable disposable liner that can be safely flushed down a toilet.

Many women, particularly those who travel extensively or work in office buildings, are forced to use public rest facilities. For the most part, public toilets are unclean and unsanitary. With the spread of communicable diseases such as acquired immunity deficiency syndrome (AIDS) many women refuse to come into bodily contact with public toilets and elect to urinate while standing. This, however, has proven to be an unsatisfactory solution to the problem in that it sometimes leads to soiling of clothing and the like.

Many different types of devices have been devised which help women urinate while in a standing position. Some of these devices, such as those described in U.S. Pat. Nos. 3,995,329 and 4,496,355, are adapted to be positioned inside the labia folds of the users vaginal cavity. The placing of foreign objects within this region is objectionable for medical and hygenic reasons particularly when the device is to be reused a number of times. These internal devices, because of their construction, are oftentimes difficult to cleanse after each use and thus pose a very real health hazard.

Urinal devices have also been developed for use by women which are adapted to be fitted externally over the mouth of the vulva in register with the uretha. These external devices are generally fabricated of plastic, hard rubber, stiff cardboard or other similarly hard materials which, when pressed securely against the woman's sensitive perineum region, can cause irritation. For the most part these devices do not contain disposable inserts or liners which might be removed and easily discarded after use. As a consequence the device must be thoroughly cleansed after each use to avoid unwanted odors and other sanitary related problems. Examples of these types of rigid reusable devices can be found in U.S. Pat. Nos. 3,613,122 and 1,407,872.

In U.S. Pat. No. 4,202,058 there is disclosed a female urinal having a rigid cup-like outer shell and a flexible inner liner that protrudes outward beyond the shell's upper opening. The liner is folded over the opening to cushion the rim area for the comfort and protection of the user. The liner is not disposable and both it and the outer shell must be cleaned after each use. The device is specifically designed to be used by a woman who is bedridden and must urinate in a supine position. U.S. Pat. No. 190,244 also describes an unlined hard rubber urinal for use by invalids or the like who cannot leave their beds.

U.S. Pat. Nos. 4,528,703 and 4,023,219 disclose reusable urinal devices that assists women in urinating while in a standing position. Each of these devices has a flexible pad or membrane surrounding the entrance of a rigid cup which contacts the vulva region. The pad prevents unwanted leakage from the cup and also is used as a wiping instrument to remove excess moisture from the contacted body region after use. In the latter patent, the pad is a multilayered horseshoe device that surrounds the rear lip of the collector. The top layer of the pad is formed of soft moisture absorbent paper and the inner layer is formed of a stiffer casein or gelatine material that disolves in water. The pad can be removed from the device after use and flushed into a sanitary drain system without harm. It should be noted that the collector does not contain a disposable liner or the like. Here again, these devices are difficult to clean and store after they have been used and are generally ill fitting and uncomfortable when being used.

SUMMARY OF THE INVENTION

It is therefore an object of the present invention to improve external reusable urinary devices for women that enable the user to safely and hygenically urinate while standing.

A further object of the present invention is to provide a woman with a sanitary, leakproof device that will enable her to urinate while in a standing position in complete comfort without danger of soiling her clothing.

A still further object of the present invention is to provide an external female urinary device that can be safely fitted over the vulva region of the user to prevent leakage and which further includes a water soluable liner that completely protects the interior surfaces of the device that can be removed from the device and flushed down a toilet.

These and other objects of the present invention are attained by means of an external female urinary device that is adapted to be positioned over the labia folds of the vulva region to collect urine and conduct the collected urine into a toilet or the like while the user is in a standing position. The device includes a rigid plastic cup of specific construction that is encapsulated within an outer blanket of soft resilient material, such as a nontoxic latex. The outer blanket is disposed over the top opening of the cup and is horizontally expanded to form a soft pliable lip that can be seated comfortably and safely against the user's body to form a water tight seal. A drain opening is provided in the bottom of the cup to enable urine collected therein to drain rapidly out of the device. The device is further provided with a liner made of gelatine that is capable of maintaining its structural integrity and body strength for some time after being wetted but which will dissolve in water within a reasonable period of time so that it can be safely disposed of in a sanitary system. The liner contains a tubular end section that passes through the bottom opening of the cup sufficient distance so that urine collected in the cup is discharged well clear of the user's clothing. The top rim of the liner is recessed in the cup well below the lip of the device so that it will not come in contact with the perineum region during use.

BRIEF DESCRIPTION OF THE DRAWINGS

For a better understanding of the present invention reference is had to the following detailed description of the present invention which is to be read in conjunction with the accompanying drawings, wherein:

FIG. 1 is a perspective view of external female urinary devices embodying the teachings of the present invention;

FIG. 2 is a perspective view of the device illustrated in FIG. 1 showing the disposable liner removed;

FIG. 3 is an enlarged side elevation in section showing in greater detail the construction of the device illustrated in FIG. 1; and FIG. 4 is a perspective view of the rigid cup that makes up the body section of the present invention.

DESCRIPTION OF THE INVENTION

Turning now to the drawings, there is shown a container generally referenced 10 that embodies the present invention. The container includes an internal cup-like body section 12 that is formed of a lightweight molded plastic of sufficient rigidity to provide a self standing structure as shown in FIG. 4. The body section is generally conical in form and includes an enlarged oval shaped top opening 13 and a smaller generally circular bottom opening 15, the side wall 17 of the cup is slightly rounded to provide a slight convex shape to the body.

The cup 12 is completely encapsulated within a rubber-like blanket 20 formed of a soft pliable material. Preferably the blanket material is fabricated of a non-toxic latex of the type widely used in the medical supply industry. The blanket extends outwardly from both the top opening of the cup and from the smaller hole 15. An expanded generally horizontally disposed lip 21 is carried by the blanket about the rim of the cup. The lip in this region is sufficiently thick to provide the lip with ample body strength so that it will normally assume the position as shown in FIG. 1. The lip, however is pliable enough so that it will conform against the vulva region of the user to provide a reliable seal thereagainst. The opposing side walls 25 and 26 of the lip have slightly concave indentations 27 and 28 formed therein to accommodate the inner thighs of the user. The indentations are centered upon the minor axis 29 of the top opening of the cup. The outer periphery of the lip is upturned into a flange 30 which during use enhances the sealing characteristics of the device.

The bottom portion of the blanket is contoured to form a short hollow neck 35 that extends outwardly from the hole 15 formed in the cup 12. As best seen in FIG. 3, the neck is turned outwardly at an angle of about 50 degrees with reference to the central axis 36 of the container. The hollow neck points in a direction that will be herein referred to as the front of the device and lies in a plane described by the major axis 37 of the cup's top opening. The interior wall of the neck blends smoothly into the interior wall of the blanket which covers the cup to provide a smooth transitional region between the inside of the neck and the inside of the cup.

The container further includes a one piece liner 40, (Fig.2) that includes a conical shaped collector 41 that is integral with an elongated tube 42. The outer periphery of the liner complements the interior contour of the blanket covered cup. The liner is adapted so that it can be inserted into the cup to provide a snug fit therein. In assembly the extended tube of the liner is passed through the hole in the neck and the collector is firmly seated against the inner wall of the container. The top edge 43 of the liner is recessed below rim 45 of the top opening (FIG. 3) of the cup so that it does not come in contact with the body of the user when the pliable lip is seated in sealing contact against the vulva region.

The liner is molded to the desired shape using gelatine as the molding material. When hardened the gelatine forms a rigid structure that will maintain its strength for some period of time after it has been initially wetted. The material, however, will dissolve completely if placed in water for longer periods of time. By adding glycerin to the gelatine, the time it takes to completely dissolve the liner can be controlled. Normally, a period of approximately one minute will be sufficient time in which to use the container and then dispose of the liner. The used liner can be deposited in a toilet where it will be completely dissolved and thus safely flushed down the sanitary drain.

The forwardly directed tube 42 extending from the liner is of sufficient length so that it will conduct urine discharged into the collector over and well clear of the user's clothing. Alternatively, a length of flexible hose 60 (FIG. 1) may be passed over the extended end of tube 42 to further lengthen the discharge passage if required.

The geometry of the collector is such that the urine directed into the container will be, under normal conditions, collected without overflowing and with a minimum amount of turbulence. The inside diameter of the tube 42 is sized so that urine received in the collector is rapidly and efficiently conducted out of the container. The convex shape of the collector, which complements the shape of the container cup, turns the incoming stream of urine and directs it downwardly into the discharge tube 42 in a stabilized relatively quiet stream.

The cup of the container measures about 3 inches along the major axis 37 and about 1½ inches along the minor axis 29 of the top opening of the cup. The depth of the container for the rim 45 to the lower opening 15 is about 2 inches. As should now be evident the apparatus of the present invention is small enough so it can be conveniently stored in a small travel kit that will fit in a woman's handbag. The disposable liners permit the device to be used repeatedly with complete safety. The device requires a minimum amount of cleansing after each use and because of its soft pliable lip design provides comfort to the user and prevents unwanted spillage that can soil garments and the like.

While this invention has been described in detail with reference to particular embodiments, it should be understood that many modifications and variations would be apparent to those of skill in the art without departure from the scope and spirit of the invention, as defined in the appended claims.

What is claimed is:

1. Apparatus for aiding a woman in urinating while in a standing position that includes a conical shaped container formed of a rigid internal cup having an oval shaped top opening and a smaller bottom opening that is situated toward the front of the cup, the central axis of said bottom opening being inclined at an angle with regard to the central axis of said top opening to point in a forward direction of said cup, a soft pliable blanket encapsulating the cup, said blanket having a lip that radially extends from and surrounds the top opening of the cup and ends in an upturned flange for sealing against the vulva region of the user, said blanket having a neck that extends outwardly from the bottom opening along said central axis of said bottom opening, said neck having an opening in its bottom portion, a disposable liner formed of a hardened water soluble gelatine having a conical shaped collector that fits snugly inside said container said liner conforming generally to the interior of said container and having an elongated discharge tube depending from the collector that is inclined at the same angle as the bottom opening in the cup, said tube passing out of the neck to form an extended spout for directing urine discharged by the user into the collector forwardly away from the user whereby the liner can be removed from the container after use and disposed of by dissolving it in a water filled sanitary drain.

2. The apparatus of claim 1 wherein the liner further contains glycerin for controlling the rate at which the liner dissolves in water.

3. The apparatus of claim 1 whereby the cup is formed of plastic and the blanket is formed of a non-toxic latex material.

4. The apparatus of claim 1 wherein said lip of the blanket further includes a raised outer flange which extends about the outer periphery of the lip.

5. The apparatus of claim 1 that further includes a flexible hose that is slidably received over the distal end of the liner tube.

6. The apparatus of claim 1 wherein the neck of the container and the tube of the liner both lie in a plane described by the major axis of the oval shaped top opening of said cup.

7. The apparatus of claim 1 wherein the cup opening measures about three inches along its major axis and about two inches along its minor axis and is about two inches deep.

8. The apparatus of claim 1 wherein the side wall of the cup is convex so as to direct incoming urine downwardly toward the bottom opening in a stabilized flow.

9. The apparatus of claim 1 wherein the lip of said blanket has a pair of opposed arcuate shaped cutouts formed therein which are centered along the minor axis of the top opening of the cup.

10. The apparatus of claim 1 wherein the top rim of the collector is recessed below the top opening in the cup so that the liner does not contact the user's body.

11. The apparatus of claim 1 wherein the tube of the liner is inclined at an angle of about 50 degrees with regard to the central axis of the cup.

12. The apparatus of claim 11 wherein the cup measures about 3 inches across the major axis of the top opening, 1½ inches across the minor axis of the top opening and is about 2 inches deep along the central axis.

* * * * *